(12) United States Patent
Chen et al.

(10) Patent No.: US 6,319,273 B1
(45) Date of Patent: Nov. 20, 2001

(54) ILLUMINATING DEVICE FOR TREATING EYE DISEASE

(75) Inventors: James C. Chen, Bellevue, WA (US); Brent Wiscombe, Mesa, AZ (US)

(73) Assignee: Light Sciences Corporation, Issaquah, WA (US)

( * ) Notice: Subject to any disclaimer, the term of this patent is extended or adjusted under 35 U.S.C. 154(b) by 0 days.

(21) Appl. No.: 09/465,545

(22) Filed: Dec. 16, 1999

(51) Int. Cl.$^7$ .................................................. A61N 5/006
(52) U.S. Cl. .............................. 607/88; 607/89; 606/4; 128/898
(58) Field of Search ..................... 606/4–6, 13, 18; 607/88–89; 128/898; 424/9.6

(56) References Cited

U.S. PATENT DOCUMENTS

| | | | |
|---|---|---|---|
| 4,907,586 | * 3/1990 | Bile et al. | 606/5 |
| 5,176,133 | 1/1993 | Czeisler et al. | 128/395 |
| 5,395,356 | 3/1995 | King et al. | 606/4 |
| 5,425,754 | * 6/1995 | Braun et al. | 607/88 |
| 5,634,920 | 6/1997 | Hohla | 606/12 |
| 5,720,772 | * 2/1998 | Eckhouse | 607/88 |
| 5,961,543 | * 10/1999 | Waldmann | 607/88 |
| 6,162,242 | * 12/2000 | Peyman | 607/88 |
| 6,200,309 | * 3/2001 | Rice et al. | 606/10 |
| 6,270,479 | * 8/2001 | Blumenkranz et al. | 424/9.61 |

* cited by examiner

*Primary Examiner*—Linda C. M. Dvorak
*Assistant Examiner*—A Farah
(74) *Attorney, Agent, or Firm*—Ronald M. Anderson

(57) ABSTRACT

A photodynamic therapy (PDT) device utilizing a non-coherent light source to activate a photoreactive agent for treating a diseased site in a patient's eye. When activated, the photoreactive agent causes a desired change in the diseased tissue of the treatment site. In one embodiment, the photoactive agent is preferentially absorbed by the diseased tissue at the treatment site, and the light from the PDT device is directed generally at the site. In another embodiment, the photoactive agent is less selectively absorbed by the diseased tissue, and the light from the PDT device is focused onto the diseased treatment site. The device preferably focuses the light emitted by a source using totally internally reflective (TIR) lenses, convergent lenses, divergent lenses, and/or deformable lenses. One embodiment incorporates a plurality of light sources of different wavebands, including a waveband that does not activate the photoreactive agent, so that the light source can be used to precisely target the focal point at the desired treatment site. Once targeted, a light source is energized to produce light in a waveband that activates the photoreactive agent and can penetrate different depths of tissue. The PDT device can be incorporated into a headset or in an ophthalmologic slit lamp. Light from the device can enter the eye through the lens of the eye, or transcutaneously via one of lateral orbital, an inferior orbital, and a superior orbital approach. In one embodiment the light sources are blue and red light emitting diodes (LEDs).

45 Claims, 9 Drawing Sheets

FIG. 7A  FIG. 7B

ILLUMINATING DEVICE FOR TREATING EYE DISEASE

FIELD OF THE INVENTION

This invention relates generally to a light therapy device for activation of photoreactive agents at one or more treatment sites within a patient's eye, and more specifically, to photodynamic therapy (PDT) devices adapted to use a noncoherent light source to activate photoreactive agents for treating macular degeneration and other ocular diseases.

BACKGROUND OF THE INVENTION

Macular degeneration is an eye disease that it is the leading cause of blindness for those aged 55 and older in the United States, affecting more than 10 million Americans. The macula is located at the center of the retina, and is responsible for the fine detailed vision required for reading, driving a car, and recognizing objects and colors. While peripheral vision is not affected, the loss of visual acuity has a significant impact on the quality of life of the person afflicted.

Two types of macular degeneration are known. The "dry" type represents 85% to 90% of the cases of macular degeneration and is most closely associated with the aging process. The "dry" type of macular degeneration is characterized by the thinning and drying out of the macula, and the formation of small yellow deposits, known as drusen, under the macula. The amount of retinal thinning caused by the drusen directly affects the loss of central visual acuity.

While the "dry" type of macular degeneration is significantly more common than the second type of macular degeneration, the "wet" type can be more devastating. The "wet" type of degeneration progresses extremely rapidly, whereas the "dry" type progresses much more gradually. The "wet" type of macular degeneration is characterized by the formation of abnormal blood vessels (known as subretinal neovascularization), which grow under the retina and macula. Leakage of blood and other fluids from these abnormal vessels cause the macula to bulge or lift up, thus distorting or destroying central vision. Scar tissue frequently forms, resulting in a permanent loss of vision. Such permanent vision loss can occur in a matter of weeks or months.

While the "wet" type of macular degeneration is less common than the "dry" type, it is significant to note that the "wet" type accounts for 90% of all cases of legal blindness.

If this disease is detected sufficiently early, immediate laser surgery can reduce the severity of vision loss associated with the "wet" type of macular degeneration. In surgically treating the problem, a laser is focused on the abnormal blood vessels and used to destroy them, thus sealing the tissue to prevent blood leakage into the eye and to prevent any additional damage to the macula. Already damaged macular tissue cannot be repaired, and the success of such laser treatments depends on destroying the abnormal vascular before excessive damage to the macular tissue has occurred.

However, laser surgery can also lead to the scarring of the macula, and additional vision loss. The abnormal blood vessels are often difficult to precisely target without causing damage to adjacent normal tissue. Various techniques are being investigated to enable more precise targeting of the abnormal blood vessels, and thereby, to reduce collateral damage to healthy tissue. One method uses a high-speed scanning pulsed laser to rapidly acquire sequences of images of the blood vessels underlying the retina, and to identify individual feeder vessels, which can then be accurately targeted for micro-laser coagulation. While this procedure offers the potential for higher precision laser targeting (thus minimizing the amount of unnecessary damage to surrounding healthy tissue), the required equipment is relatively expensive.

Indocyanine green dye has been used to pinpoint abnormal neovascularization beneath the macula. The dye targets and sensitizes the abnormal vessels to help focus laser energy used in some types of eye surgery. However, the intensity of the laser light employed in the process can still cause damage to non-target normal tissue.

PDT techniques show significant potential in treating these eye diseases. In PDT, a light activated compound is administered to the patient and tends to concentrate in the areas of neovascularization. This absorbed compound is then activated by directing a low-power laser light into the patient's eye and onto the neovascularization areas. When activated, the compound undergoes a chemical change, producing free radicals and/or other products that destroy the abnormal tissue. Miravant of Santa Barbara, Calif. is testing a PDT drug called PURLYTIN™ (tin ethyl etiopurpurin), while QLT Phototherapeutics of British Columbia, Canada (with its partner Ciba Vision, Atlanta, Ga.) is testing a PDT drug VERTEPORFIN™ (a liposomal benzoporphyrin derivative) for treating ocular diseases. PDT can be relatively selective in destroying only the abnormal neovascularization, and the use of relatively low power laser light to activate the PDT drugs minimizes the risk to surrounding healthy macular tissue.

Although PDT shows significant potential in treating macular degeneration, the laser equipment required for carrying out the above-described PDT is again relatively expensive. The demand for an effective treatment of macular degeneration is high (note that over 10 million North Americans suffer from macular degeneration), and expensive equipment can greatly reduce the availability of such treatment. It would be desirable to develop low-cost apparatus, and methods for the use of such apparatus, to provide greater access to PDT treatment of macular degeneration. The use of a non-coherent light source to activate a photoactive compound offers significant cost advantages over the use of a laser light source.

SUMMARY OF THE INVENTION

In accord with the present invention, apparatus and a method are defined for using light in treating a disease of the eye. The apparatus includes an electrical power source, at least one non-coherent light source coupled to the power source, and at least one focusing lens adapted to convey light emitted by the non-coherent light source to the eye. In one embodiment, the apparatus includes a mirror positioned adjacent to one or more light sources so as to reflect light from the light source through the focusing lens. The focusing lens is disposed between the light source and the eye.

Preferably, the light source is either a light emitting diode (LED), an incandescent bulb, or a cold cathode fluorescent tube. If one or more LEDs are used for the light source, they preferably emit light that is either red or blue, or both. The light source can alternatively comprise a laser diode array that generates non-coherent light.

In another embodiment, the apparatus is mounted on a headset. The headset preferably includes a frame like that used for eyeglasses.

The one or more focusing lens comprises a divergent lens, a convergent lens, and/or a totally internally reflective (TIR)

lens. In one embodiment, the focusing lens focuses light from the light source onto a macular region of the eye. In another embodiment the apparatus includes a filter that incorporates a first portion that blocks a waveband of light emitted by the light source, and a second portion that transmits the waveband of light emitted by the light source. The filter is disposed between the light source and the focusing lens. The size and shape of an area illuminated by the light that is filtered and directed on a diseased treatment site corresponds to the size and shape of the second portion of the filter. The size and shape of this area of light can be selectively varied by selecting a filter with an appropriately sized and shaped second portion.

In one embodiment, either or both the first and second portions change from a first state in which the portion transmits the waveband of light, to a second state in which the waveband of light from the light source is blocked. This change of state is responsive to an electrical stimulus. A liquid crystal material or a piezoelectric ceramic material is preferably used to fabricate the filter.

The location within the eye of the focal point of light emitted by the light source is selectively varied by changing the position of either the light source or the focusing lens. In an embodiment that includes a plurality of focusing lenses of different focal lengths, the disposition of the focal point within the eye is varied by selecting an appropriate one of the plurality of focusing lenses.

In an embodiment in which the focusing lens is fabricated from a deformable material, the focal point is selectively adjusted by means that deform the focusing lens, disposed adjacent to a periphery of the focusing lens. Means such as a mechanical actuator, a hydraulic actuator, or an electrical actuator are employed. The location within the eye of the focal point is thus varied.

Yet another embodiment includes a filter that transmits specific wavebands of light generally corresponding to the activation wavebands of the PDT drug that has been administered. Such a filter is selectively moveable between a first position in which it is outside an optical path of the light source, and a second position in which it is in the optical path.

A further embodiment includes a plurality of light sources. A first light source emits a wavelength of light that does not activate the PDT drug that has been administered, and a second light source emits a wavelength that does. Preferably, the first and second light sources are disposed such that a first focal point of the first light source substantially overlaps a second focal point of the second light source. Thus, the position of the first focal point can be targeted at the diseased treatment site in the eye without activating the PDT drug, and the second light source can then be energized to activate the PDT drug at the diseased treatment site, without activating any PDT drug located in other sites of the eye. In this manner, the first light source is used to help pinpoint the target zone of the second light source to prevent collateral damage, Another embodiment includes a first light source that emits light in a waveband characterized by not penetrating deep into tissue, and a second light source that emits light in a waveband that characteristically penetrates substantially deeper into tissue.

BRIEF DESCRIPTION OF THE DRAWINGS FIGURES

The foregoing aspects and many of the attendant advantages of this invention will become more readily appreciated as the same becomes better understood by reference to the following detailed description, when taken in conjunction with the accompanying drawings, wherein:

FIGS. 7A and 7B illustrate filters that each result in a different size and shape of the focal point for use in conjunction with the fifth embodiment of the present invention as illustrated in FIG. 7;

DESCRIPTION OF THE PREFERRED EMBODIMENT

Figure 1:
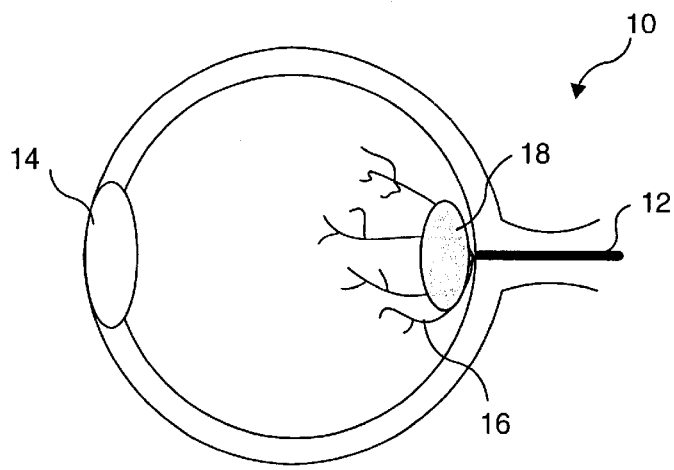
FIG. 1 is a schematic view of an eye, illustrating several regions of the eye that relate to the present invention.

In FIG. 1, an eye 10 is schematically illustrated; the Figure is not intended to show all of the anatomical structures of an eye, but rather to illustrate only the structures of interest related to PDT in accord with the present invention. The eye includes a lens 14, as well as a normal vasculature 16, a macula 18, and an optic nerve 12. As noted above in the Background of the Invention, age-related macular degeneration is an eye disease that occurs in two variants: the wet type and the dry type. The dry type is characterized by a thinning of macula 18, and the formation of drusen, a yellow material that forms in the macula. The wet type is characterized by the growth of abnormal vascular within the macula. This abnormal vascular growth damages the tissue of the macula and typically results in a loss of vision. The wet type variant is amenable to treatment using PDT. Studies have shown that photodynamic drugs such as verteporfin (developed by QLT Phototherapeutics Inc. and CIBA Vision Corporation) and purlytin (developed by Miravant of Santa Barbara, Calif.) may be useful in treating eye diseases such as age-related macular degeneration when the drugs are activated with non-thermal laser light.

It is believed that non-coherent light sources may also be used to activate PDT compounds to treat diseases of the eye. The use of a non-coherent light source has the potential of reducing the cost of the associated treatment apparatus, and reducing the risk of damage to non-target tissue in the macula that may occur when even low-powered lasers are used.

Figure 2:
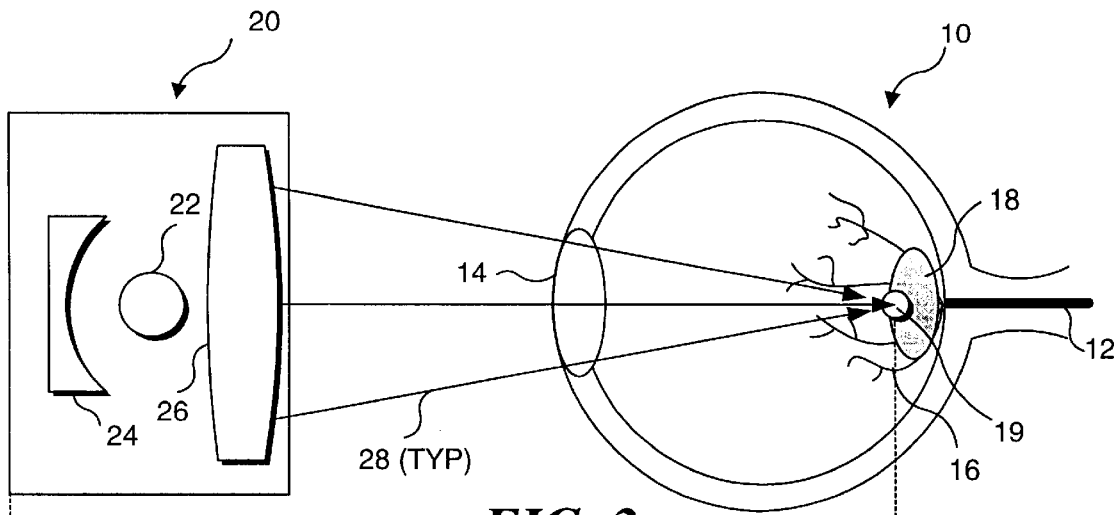
FIG. 2 is a schematic view of a first embodiment in accord with the present invention being used to deliver non-coherent light to a treatment site in the eye.

Accordingly, a PDT device 20 is illustrated in FIG. 2 that includes a non-coherent light source 22. PDT device 20 also includes a convergent lens 26, a light emitting diode (LED) non-coherent light source 22, and a concave reflector 24. However, other types of non-coherent light sources may be used, such as incandescent bulbs. The non-coherent light source emits light having a waveband corresponding to the absorption or activation waveband of the PDT drug being used. The PDT drug that is employed is selected because of its characteristic of being concentrated in the abnormal vascular of the macular region in eye 10. Referring once again to FIG. 2, light rays 28 are shown passing through lens 14 and converging at a focal point 19 within macula 18. Focal point 19 may be targeted at a desired location within macula 18 (or some other region of interest within the eye) by manipulating the position and/or orientation or focus of PDT device 20.

Figure 3:
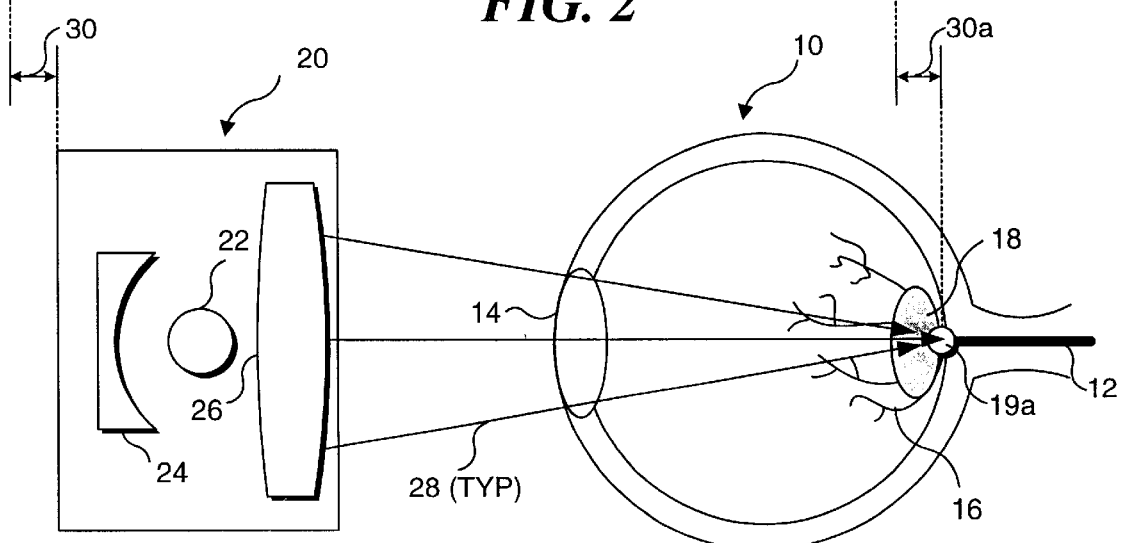
FIG. 3 illustrates how a focal point of the light delivered by the first embodiment can be shifted to a different treatment site in the eye by changing the position of the device.

FIG. 3 illustrates a PDT device 20 which has been shifted by a lateral adjustment 30. Focal point 19 has experienced a corresponding lateral shift 30a to a new position 19a. Thus, by manipulating the position and/or orientation, and/or focus of PDT device 20, a practitioner can selectively target discrete locations within macula 18 or other places within the eye. Furthermore, it should be noted that because light source 22 is non-coherent and of relatively low power, compared to coherent laser sources, there is very little danger of damage to non-target tissue. Not only is light source 22 of such low power as to be incapable of causing tissue damage in and of itself, the PDT drug that is preferably used in association with PDT device 20 can be selected for its characteristic of selectively concentrating within the abnormal vascular of the macular region. Alternatively, it is contemplated that targeted PDT drugs may be produced that preferably link to specific types of cells or cell components so as to ensure that the PDT drug is primarily concentrated in the abnormal tissue to be destroyed by PDT. In any case, there will be little PDT drug within other structures of the eye that might be activated by light source 22, and damage to other structure in the eye that are normal should not occur.

Figure 4:
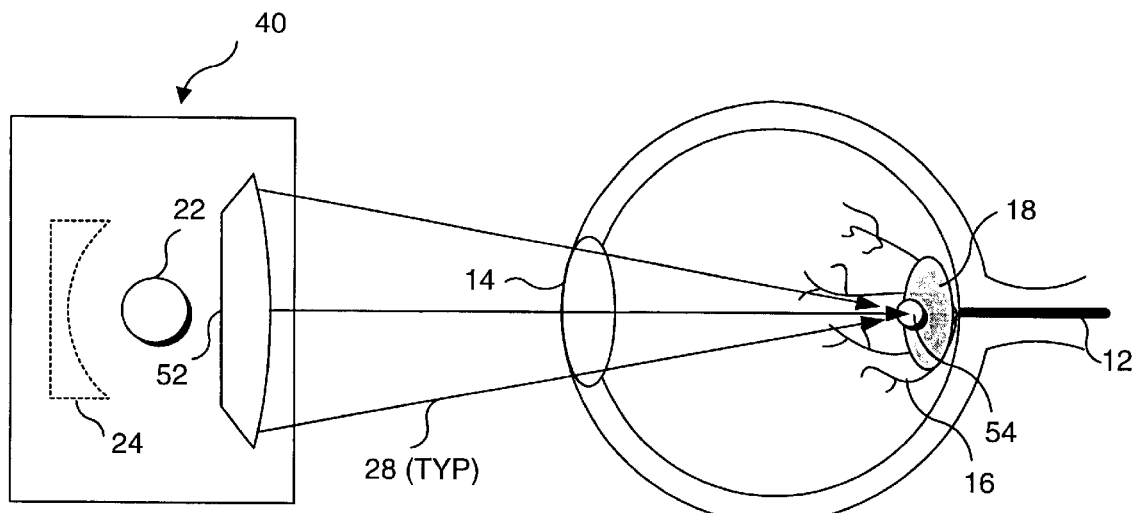
FIG. 4 is a schematic view of a second embodiment of the present invention that incorporates a TIR lens being used to deliver non-coherent light to a treatment site in the eye.

FIG. 4 illustrates a second embodiment. A PDT device 40 is shown administering light rays 28 to a focal point 54 in macula 18. PDT device 40 incorporates a TIR lens 52 in place of the convergent lens that was used in the first embodiment discussed above. As noted previously, light source 22 is preferably an LED, although other types of non-coherent light sources may be used. A reflector 24 can optionally be included in PDT device 40. As described above with respect to PDT device 20, PDT device 40 can be similarly manipulated to change the position of focal point 54 to which the light emitted by light source 22 is directed.

Figure 5:
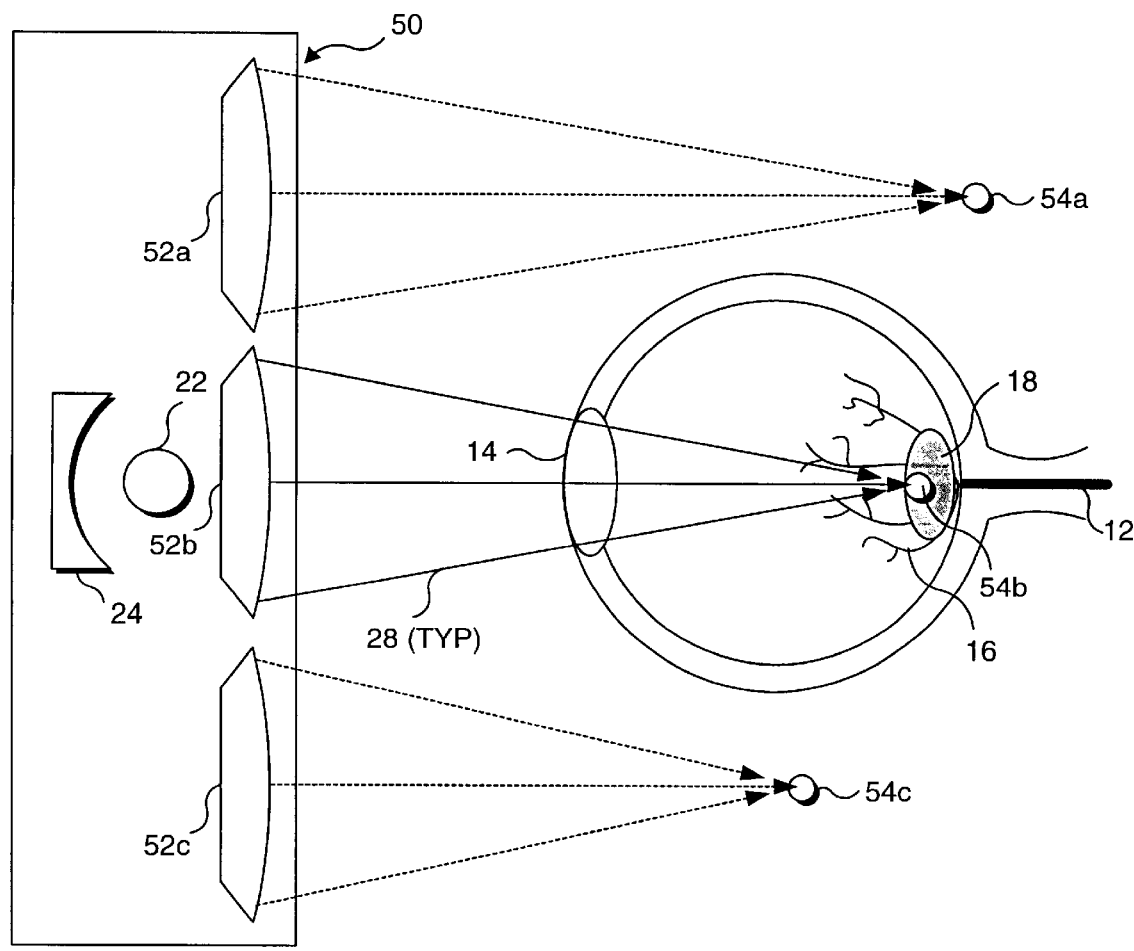
FIG. 5 is a schematic view of a third embodiment of the present invention that incorporates a plurality of TIR lenses, and the different focal points associated with each lens.

FIG. 5 illustrates a PDT device 50 in which the focal point can be adjusted without repositioning the PDT device. PDT device 50 incorporates a plurality of TIR lenses 52a, 52b, and 52c, each of which provides a different focal point. It should be noted that the convergent lens of PDT device 20 could also be incorporated in PDT device 50. Also it should be noted that the number of lenses that can be incorporated into PDT device 50 is not limited to only three. More lenses arranged in a two-dimensional array, for example, could be used to provide greater flexibility in selecting a particular focal point without repositioning PDT device 50. PDT device 50 incorporates a light source 22 and a reflector 24. As noted with regard to PDT device 40, reflector 24 is optional and can be omitted. In one embodiment of PDT device 50, TIR lenses 52a, 52b, and 52c are moveable, and can be selectively positioned in front of light source 22. TIR lens 52a is has a focal point 54a, while TIR lens 52b has a focal point 54b, and TIR lens 52c has a focal point 54c. Thus, without repositioning PDT device 50, a plurality of different focal points can be achieved by moving an appropriate one of the TIR lenses in front of light source 22.

Figure 6:
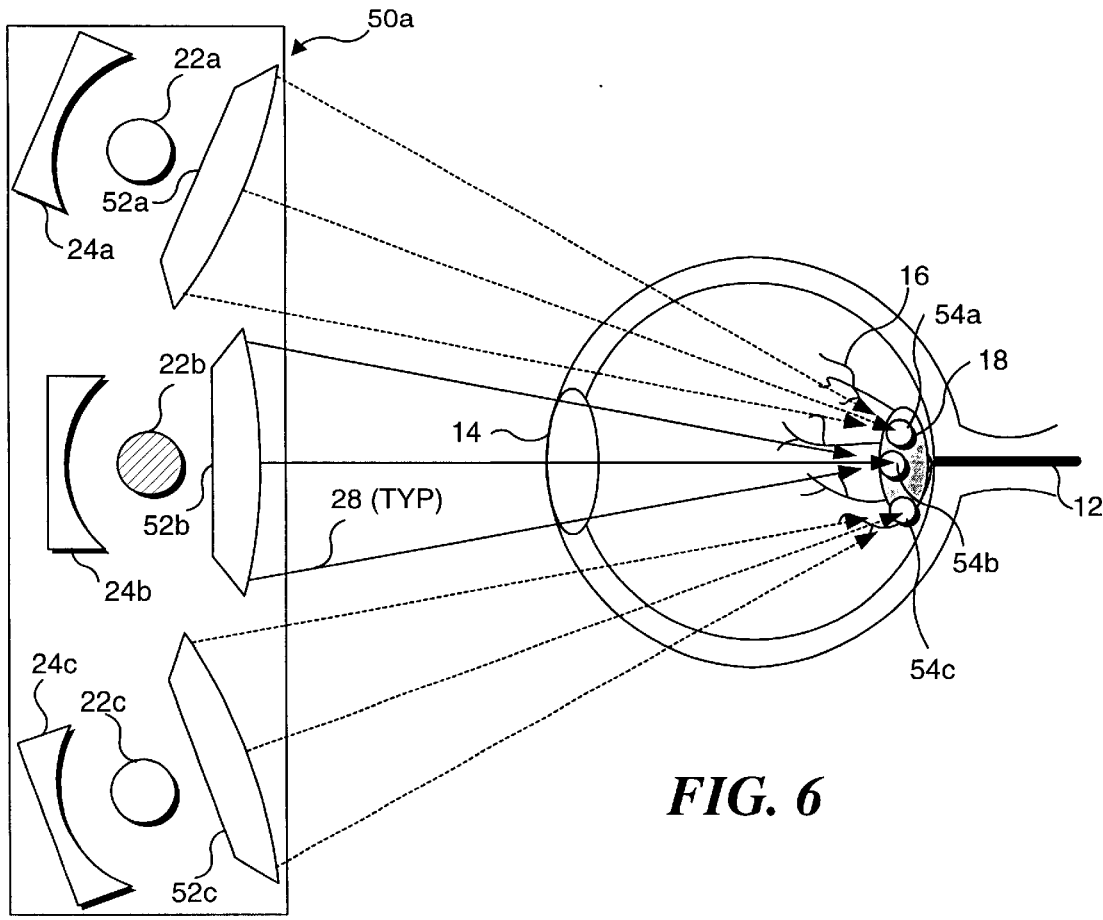
FIG. 6 is a schematic view of a fourth embodiment of the present invention that incorporates a plurality of TIR lenses, and the different focal points associated with each lens.

A second embodiment of a PDT device 50a that provides a plurality of different focal points without requiring repositioning of the PDT device is illustrated in FIG. 6. In PDT device 50a, TIR lenses 52a, 52b, and 52c are not moveable. Instead, PDT device 52a incorporates a plurality of light sources 22a, 22b, and 22c, one for each TIR lens 52a, 52b, and 52c. Reflectors 24a, 24b, and 24c can optionally be included, one for each of the light sources. In PDT device 50a, focal point 54a, 54b, or 54c is selected by energizing light source 22a, 22b, or 22c that is associated with the desired focal point. As illustrated in FIG. 6, light source 22b has been energized, resulting in focal point 54b being achieved. While not shown, it is envisioned that a similar device can be constructed using a plurality of TIR lenses in association with a single light source and a plurality of reflectors that enable light rays from the light source to be selectively directed through the TIR lens that corresponds to the desired focal point.

Figure 7:
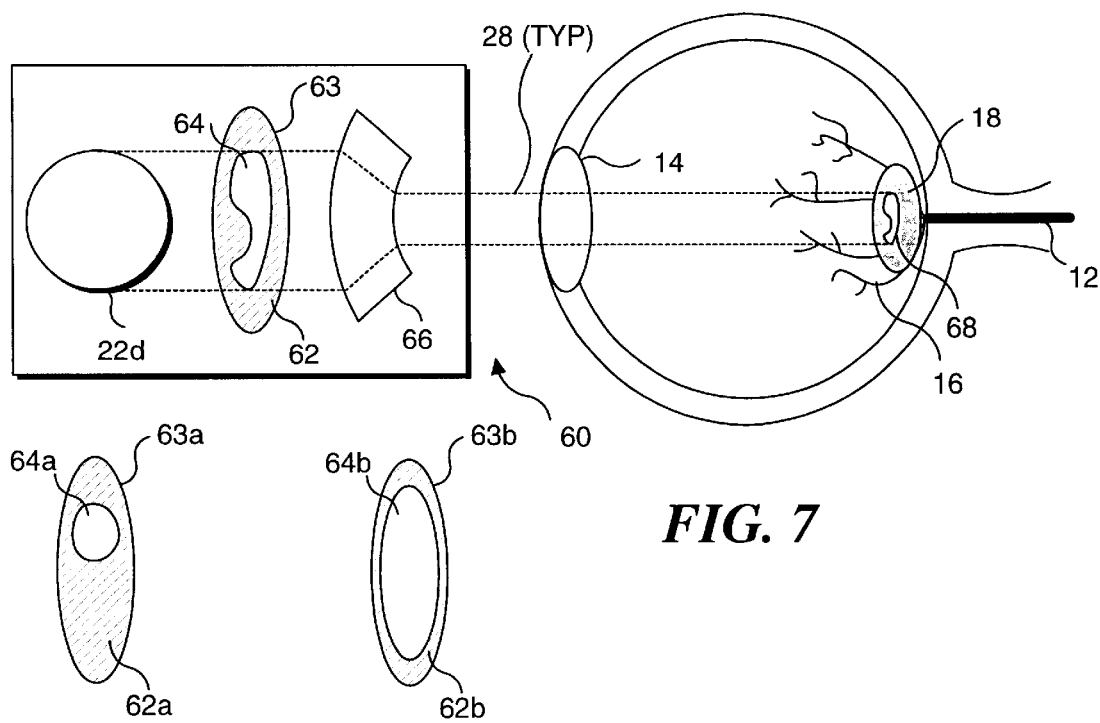
FIG. 7 is a schematic view of a fifth embodiment of the present invention that incorporates a complex lens and a filter which changes the size and shape of the focal point being used to deliver non-coherent light to a treatment site in the eye.

In FIG. 7, a PDT device 60 incorporates a light source 22d, a filter 63, which includes an opaque region 62 and a transparent region 64, and a diverging lens 66. Light rays from light source 22d are blocked by opaque region 62, casting a correspondingly shaped shadow 68 on the treatment site within the eye. Light not blocked by the opaque region is transmitted through transparent region 64 and into the eye. Those of ordinary skill in the art will readily understand that the size of shadow 68 relative to transparent region 64 can be varied by selecting an appropriate focus for diverging lens 66. As discussed above, the position of the focal point and of shadow 68 relative to macula 18 can be adjusted by repositioning PDT device 60. Light source 22d is preferably an LED and can include, if desired, a reflector (not shown) similar to the reflectors described in the preceding embodiments.

FIGS. 7A and 7B illustrate filters 63a and 63b, which incorporate different shapes of transparent regions 64a and 64b and opaque regions 62a and 62b. Thus, by replacing filter 63 with a different filter, the shape of the shadow at the focal point of the PDT device can readily be varied to treat different shapes of abnormal tissue at the treatment site within the patient's eye.

Figure 8:
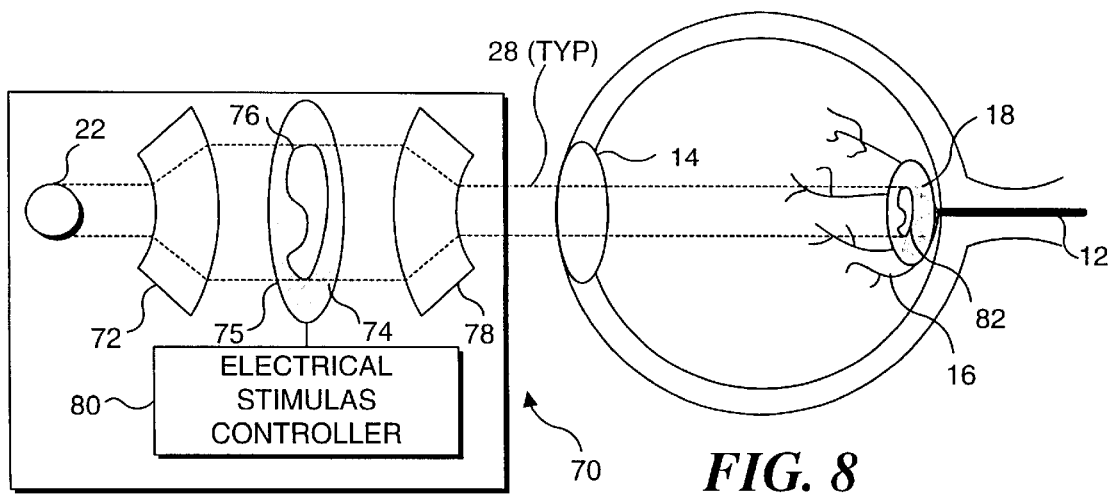
FIG. 8 is a schematic view of a sixth embodiment of the present invention that incorporates two complex lenses and a filter, which changes the size and shape of the focal point in response to an electrical stimulus, being used to deliver non-coherent light to a treatment site in the eye.

FIG. 8 illustrates a PDT device 70 in which the shape of the focal point can be varied without replacing the filter element. PDT device 70 includes a light source 22, a diverging lens 72, a filter element 75, which includes a transparent region 76 and an opaque region 74, and a diverging lens 78. PDT device 70 also includes an electrical stimulus controller 80. As noted above, the choice of divergent lens 72 and divergent lens 78 can provide a desired focal point 82, which is useful in treating diseases on macula 18. Filter element 75 is preferably fabricated from a material that changes its index of refraction or its transparency with an applied heat or in response to an electrical stimulus. The techniques used to produce liquid crystal displays (LCDs) can also be used to create a mask that can selectively be controlled to block light transmission through a portion of the filter element. The mask can be made so that the desired shape of light or of the shadow at the focal point is achieved when the mask is energized to block some of the light going through the lens. The mask can also include a plurality of pixels or regions that are electrically controlled so as to alter the pattern of light transmission through the mask as is typically done in a LCD. In this manner, the shape or pattern of the light blocking pixels can be changed as desired in order to create different light/shadow patterns at the focal point of the PDT device. Ceramic materials (referred to as PZT materials) are also readily available that can be used to create a light mask. These ceramic materials appear transparent to light until an electrical stimulation is applied, at which time, they are rendered partially or completely opaque. The electrical stimulation can be applied through a transparent, indium oxide conductive electrode that is applied to the surface of the PZT material in a predefined electrode pattern similar to that employed for the LCD mask pattern.

Figure 9:
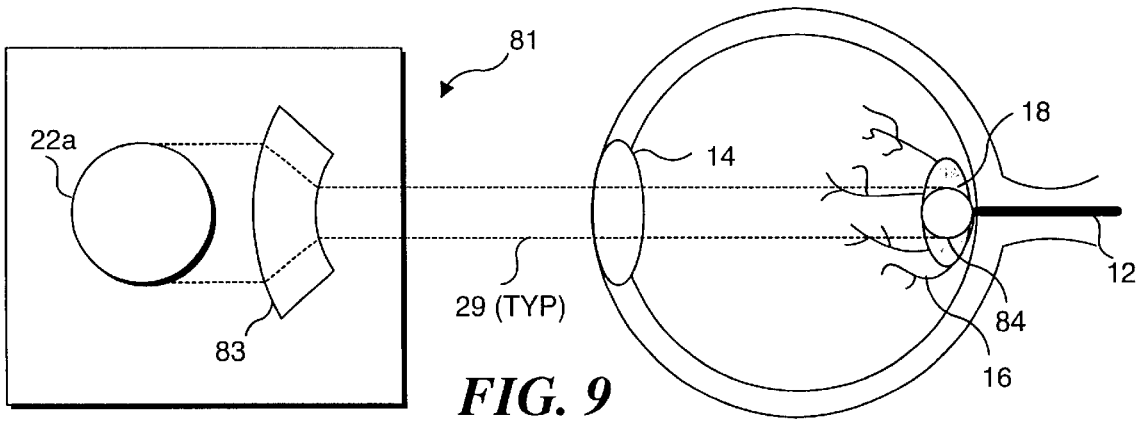
FIG. 9 is a schematic view of a seventh embodiment of the present invention that incorporates a deformable lens, which changes the size and shape of the focal point in response to a deforming force, being used to deliver non-coherent light to a treatment site in the eye.
Figure 9A:
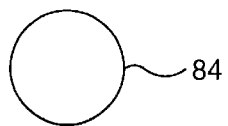
FIG. 9A is an enlarged cross-sectional view of the focal point delivered by the seventh embodiment of the present invention when the deformable lens is not effected by a deforming force.
Figure 10A:
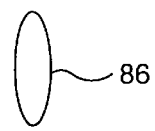
FIG. 10A is an enlarged cross-sectional view of the focal point delivered by the seventh embodiment of the present invention when the deformable lens is effected by a deforming force.
Figure 10:
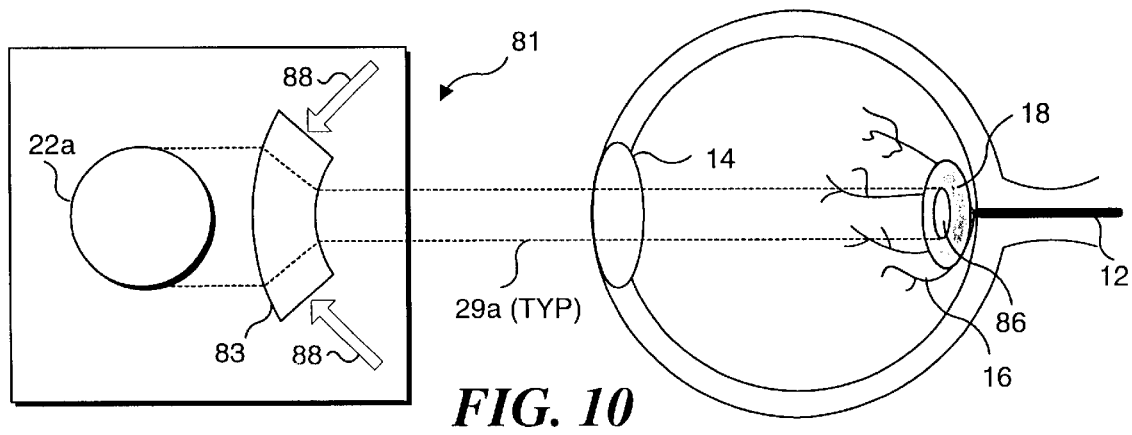
FIG. 10 is a schematic view of the seventh embodiment of the present invention in which a force has been applied to the deformable lens resulting in a change in the size and shape of the focal point being used to deliver non-coherent light to a treatment site in the eye.

FIGS. 9, 9A, 10, and 10A illustrate a PDT device 81, which changes the shape of the focal point using a different property. PDT device 81 incorporates a light source 22a and a convergent lens 83. Convergent lens 83 is fabricated from a material that can be deformed sufficiently without damaging the lens. Lens 83 is selectively deformable, to change the pattern of light passing through the lens, when focused on a treatment site or to alter the focal point. As lens 83 is deformed, the light traveling through the lens is redirected to form an elongate oval pattern at the focus of the lens. Pressure can be exerted on the outer periphery of the lens to cause the lens deformation resulting in a desired light pattern. Alternatively, mechanical forces can be applied to the outer surface of lens 83 to cause the lens to distort or deform, thereby producing the desired light pattern on a treatment site inside the eye. This mechanical force can be applied to the lens by activating piezoelectric crystals, or by miniature pneumatic/hydraulic cylinders, or simply by use of electrically actuated (motor driven) screws, clamps, or lever devices. In FIG. 9, lens 83 is undistorted and a focal point 84 represents a circular light pattern. It should also be noted that the position of focal points 84 and 86 can be manipulated by moving PDT device 81. Furthermore, reflective elements similar to reflectors 24, as illustrated in the previously discussed Figures, can be included in PDT device 81.

Figure 11A:
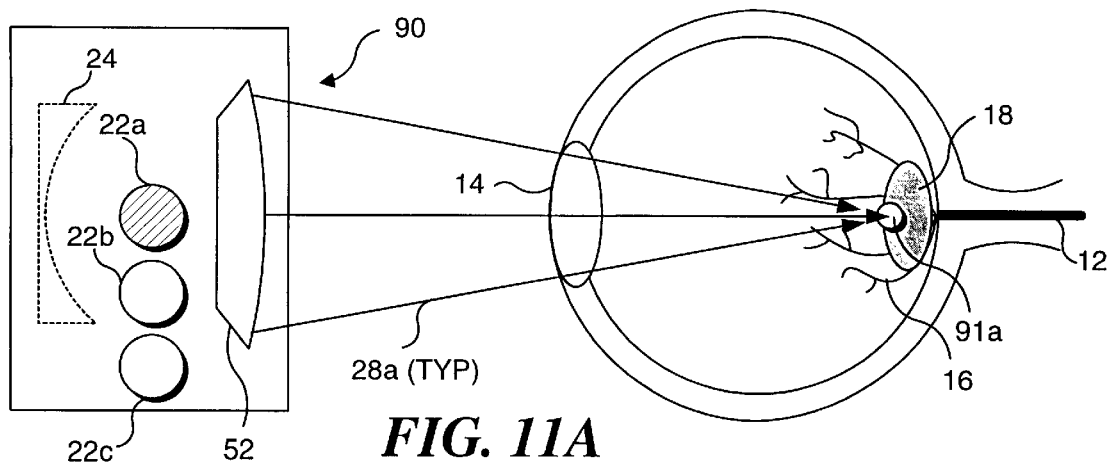
FIG. 11A is a schematic view of an eighth embodiment of the present invention that incorporates a plurality of light sources being used to deliver non-coherent light, whose wavelength will not activate a photoactive agent, to a treatment site in the eye.
Figure 11B:
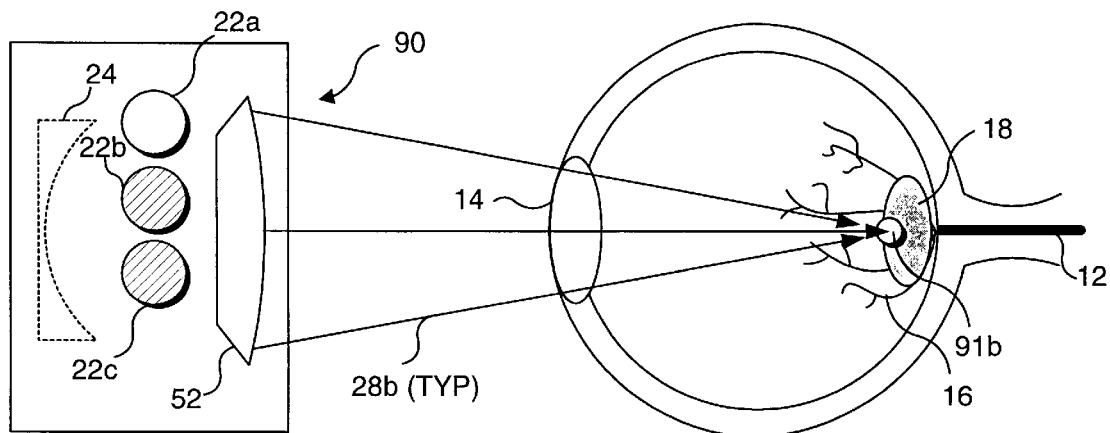
FIG. 11B is a schematic view of the eighth embodiment of the present invention being used to deliver non-coherent light, whose wavelength will activate a photoactive agent, to a treatment site in the eye.
Figure 11C:
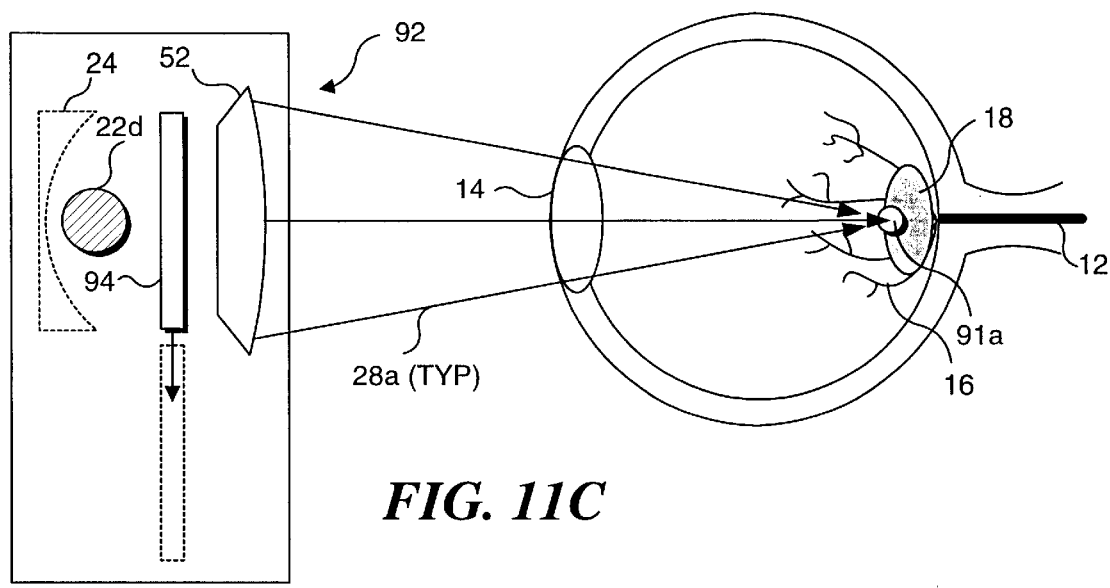
FIG. 11C is a schematic view of a ninth embodiment of the present invention that incorporates a plurality of filters, which can be used to modify the wavelength of light emitted by the light source, being used to deliver non-coherent light to a treatment site in the eye.

FIGS. 11A, 11B, and 11C illustrate PDT devices that allow a practitioner to use a non-activating wavelength of light to verify the position of the focal point relative to the macula, and then to selectively transmit a desired wavelength of light to the focal point. PDT drugs are known that are activated using either blue or red light of a wavelength corresponding to the absorption waveband of the photoreactive agent drug. Blue light sensitive PDT drugs typically have relatively large absorption peaks, which enable far less drug to be given to achieve the same therapeutic effect. The reduced dosage of the PDT drug in turn reduces side effects, such as elevated dermal photosensitivity. Another advantage of using PDT drugs that are activated by blue light is that light of this waveband penetrates only a short distance into normal tissues surrounding the treatment site. PDT drugs activated by red light are preferred if the treatment site is obscured by tissue or physiological structures, since the longer wavelength light more readily penetrates such tissue to a greater depth.

With reference to FIGS. 11A and 11B, a PDT device 90 includes a non-PDT drug activating light source 22a, a PDT drug activating light source 22b, and a PDT drug activating light source 22c having a different wavelength than light source 22b. PDT device 90 also includes a TIR lens 52, and optionally includes a reflector 24. It should be noted that convergent lenses as discussed with respect to other embodiments could also be used instead of TIR lens 52 as shown. In FIG. 11A, light source 22a is energized and the practitioner can observe the condition of the eye at a focal point 91a, to determine how best to render PDT, and to select a focus for the PDT that will be provided when the other light sources are activated. Because light source 22a produces a wavelength that does not activate the PDT drug that has been administered to the patient, the practitioner is able to position PDT treatment device 90 such that the position of focal point 91a corresponds to the desired treatment area within macula 18 (or other region of interest). Because light source 22a is non-coherent, and does not activate the PDT drug, continued illumination with light source 22a while the PDT is ongoing has no adverse effect on the patient. In FIG. 11B, light source 22a has been de-energized, and light sources 22b and 22c have been energized. The wavelengths of light rays 28b overlap the absorption or activation waveband of the PDT drug administered to the patient. Accordingly, the light converging at focal point 91b activates the PDT drug and initiates the treatment process. Light sources 22b and 22c are selectively energizable, such that either or both can be energized as desired. As discussed above, light sources 22b and 22c preferably are LEDs, which generate light in the blue waveband and red wavebands, respectively. The various light sources are moved into the position behind TIR lens 52 when activated to provide light on the treatment site.

FIG. 11C illustrates a PDT device 92 that also enables a practitioner to use a non-PDT drug activating wavelength of light to insure that focal point 91a is located corresponding to the target of interest, and then to selectively transmit wavelengths of light which activate the PDT drug. PDT device 92 incorporates a light source 22d, which emits a waveband of light that activates the PDT drug, as well as a waveband of light that does not. PDT device 92 also includes TIR lens 52, and optionally includes a reflector 24. As noted above, other types of lenses may be beneficially provided in PDT device 92. PDT device 92 also includes a filter 94. Filter 94 is selected to modify the wavelength of light emitted by light source 22d, such that the light passing through TIR lens 52 and converging at focal point 91 a has been filtered to exclude the waveband that activates the PDT drug. As illustrated in FIG. 11C, filter 94 is positioned to filter the light emitted by light source 22d. Thus, focal point 91a does not include the wavelength of light that activates the PDT drug, and in this configuration, treatment device 92 can be focused at the desired target of interest without activating the PDT drug. When filter 94 is moved out of the optical path between light source 22d and TIR lens 52, the wavelengths of light converging at focal point 91a include the wavelengths corresponding to the activation waveband of the PDT drug, and treatment is rendered. As noted above, filter 94 preferably modifies the wavelength of light emitted by light source 22d to eliminate light in the red and blue spectrums.

It is envisioned that the PDT devices described in the above embodiments can be beneficially incorporated into a lightweight headset that can be worn by a patient, or incorporated into a more traditional slit lamp similar to those used by optometrists. FIGS. 12, 13, 14, and 15 illustrate different embodiments of a headset that can be worn by a patient. FIG. 16 illustrates how the PDT devices described above are incorporated into a traditional, permanently fixtured slit lamp.

Figure 12:
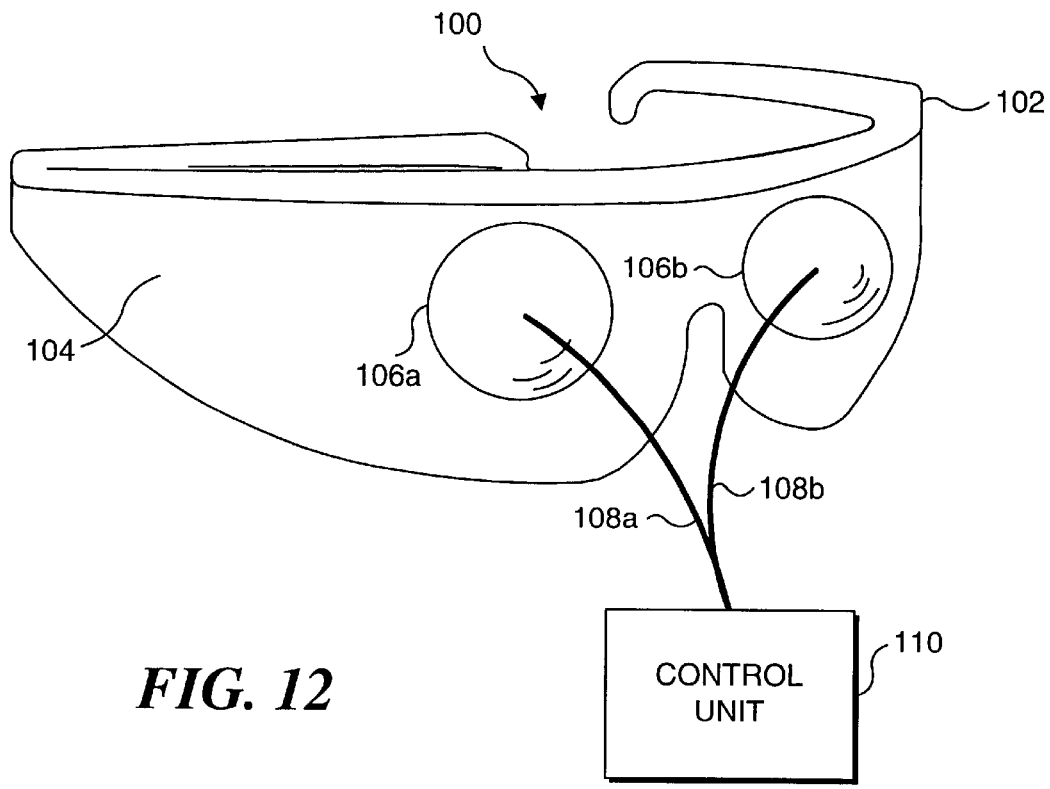
FIG. 12 is a schematic view of a headset that incorporates one of the embodiments of the present invention.

FIG. 12 illustrates a PDT headset 100. PDT headset 100 appears much like a conventional pair of wraparound eyeglasses, but includes PDT devices 106a and 106b disposed on the front of the lenses, adjacent to the patient's eyes. A frame 102 is preferably fabricated from metal, and if desired, can be coated with a plastic material as is commonly done for prescription eyeglasses, or can be fabricated entirely of plastic. A lens 104 is preferably an opaque, shatter resistant plastic material. While lens 104 could be transparent, use of an opaque material for lens 104 enables the patient's eyes to dilate by reducing incident light on the eyes and helps to prevent untargeted light rays from reaching the patient's eyes. It should be noted that PDT devices 106a and 106b are not obstructed by opaque lens 104, but instead are either fitted over a window (not shown) in the lenses or the portion of lens 104 covered by PDT devices 106a and 106b are transparent and not opaque.

Figure 13:
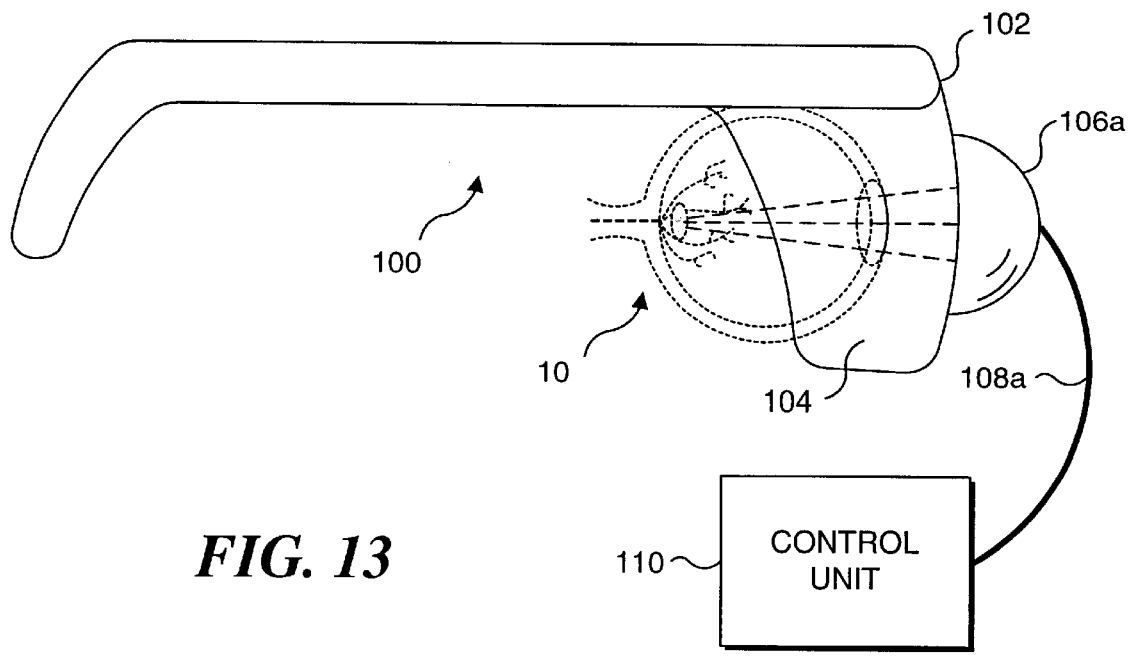
FIG. 13 is a schematic view of the headset of FIG. 12 being used to deliver non-coherent light to a treatment site in the eye.

Control cables 108a and 108b connect PDT devices 106a and 106b, respectively, to a control unit 110. Control unit 110 enables the practitioner to selectively activate the light sources in either or both PDT devices 106a and 106b. FIG. 13 illustrates a side view of PDT headset 100. PDT device 106a has been selectively energized, and is being focused on the macula of eye 10. It is envisioned that PDT device 106a and 106b can beneficially include the elements of any of the embodiments described above. However, PDT devices 106a and 106b preferably enable the focal point of the light being administered to the treatment site within the eye to be adjusted without requiring movement of PDT headset 100, and those embodiments of the PDT devices discussed above that permit such functionality are preferred. While PDT headset 100 can be manipulated somewhat while being worn by a patient, it is more convenient if the light sources in PDT devices 106a and 106b can be focused on the treatment site in the patient's eyes without requiring such manipulation.

Figure 14:
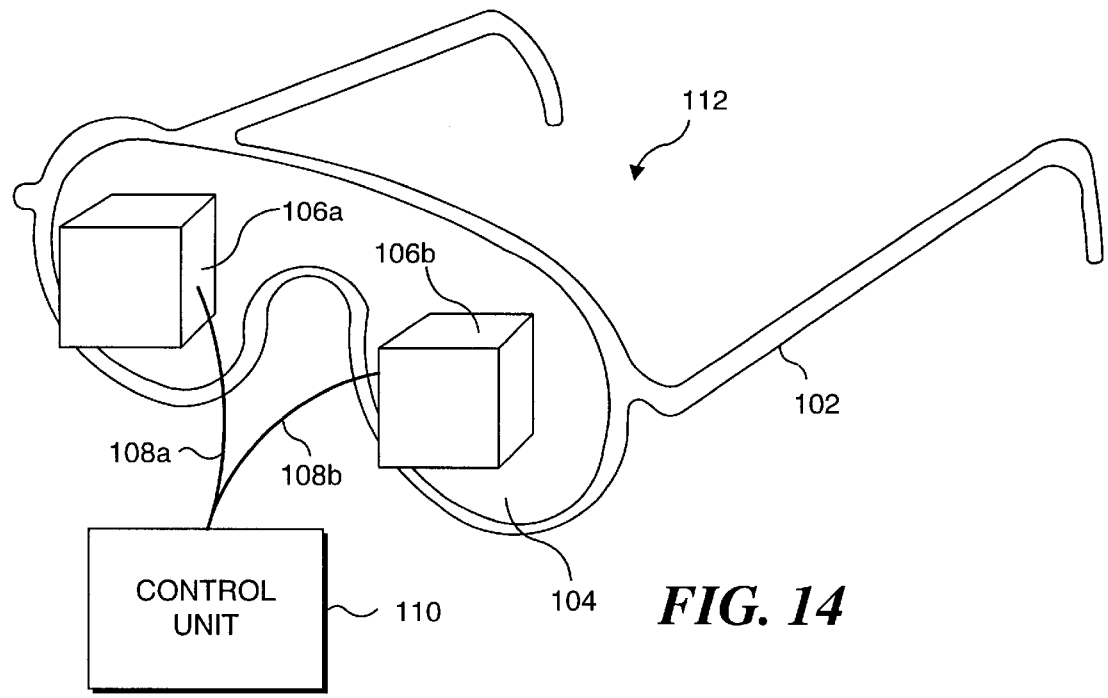
FIG. 14 is a schematic view of another type of headset that incorporates one of the embodiments of the present invention.
Figure 15:
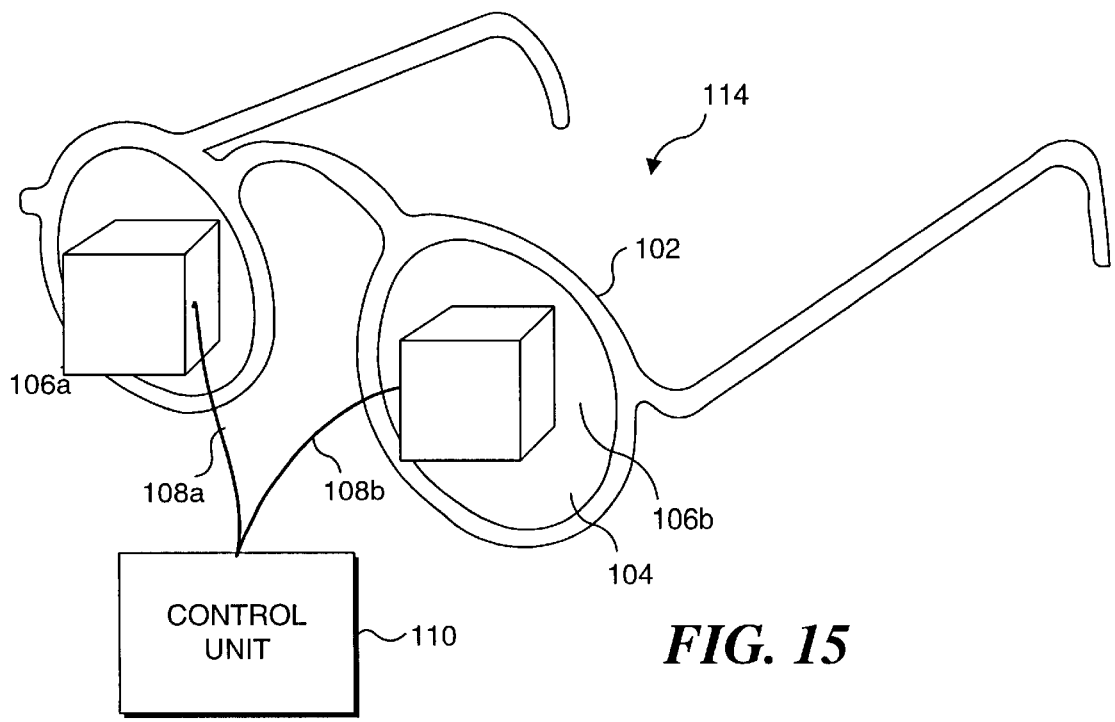
FIG. 15 is a schematic view of yet another type of headset that incorporates one of the embodiments of the present invention.
Figure 16:
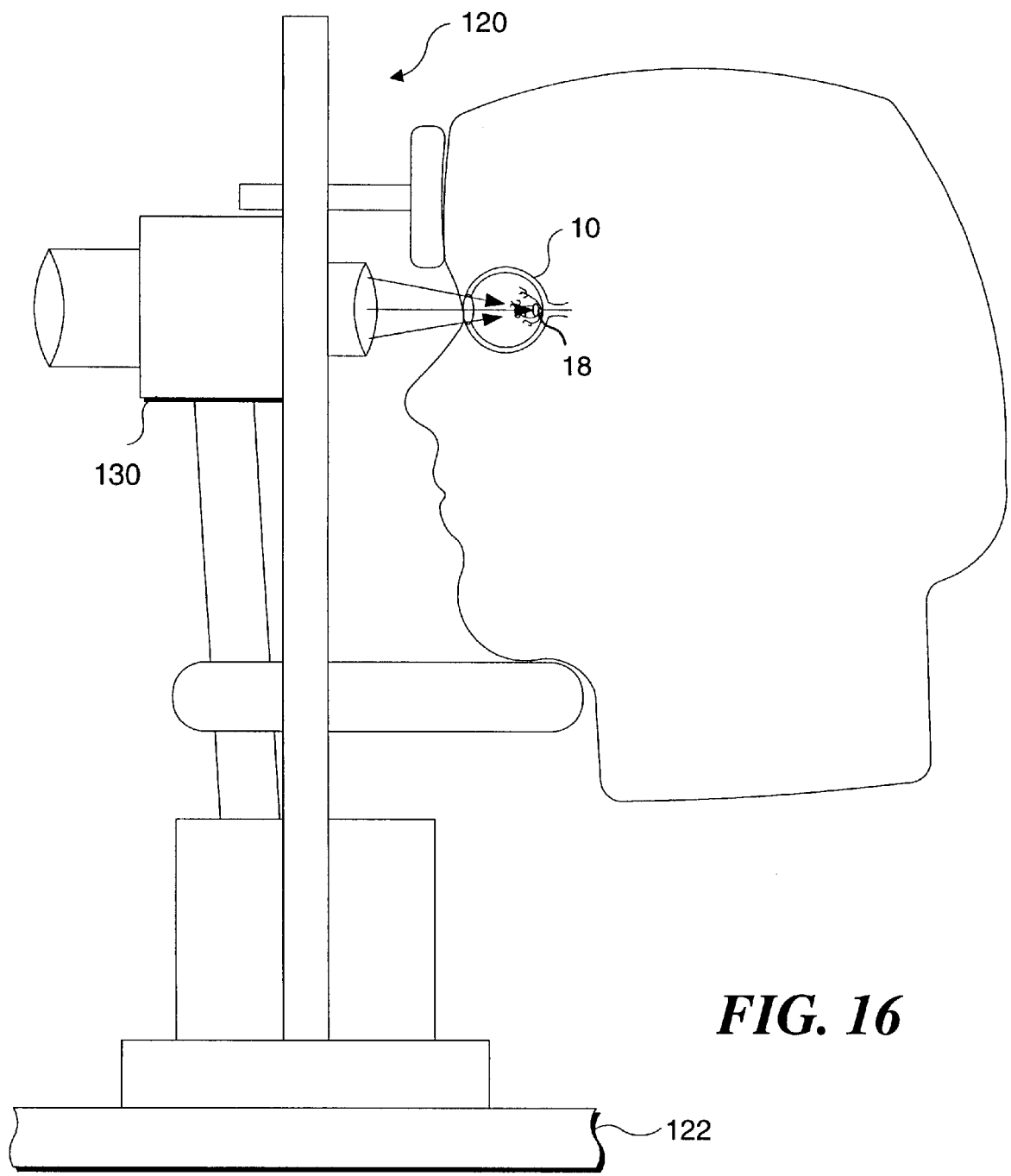
FIG. 16 is a schematic view of a slit lamp that incorporates one of the embodiments of the present invention being used to deliver non-coherent light to a treatment site in the eye.

FIGS. 14 and 15 illustrate different embodiments of a PDT headset 112 and 114, respectively. These devices are identical in operation to PDT headset 100, and illustrate that a plurality of different headset designs are possible within the scope of the present invention. Preferably, PDT headsets 100, 112, and 114 are constructed of lightweight and durable materials, not prone to breakage, and have a shape and size selected so that the headsets are comfortable when worn by a patient. As much as possible, the elements required for the operation of PDT devices 106a and 106b are incorporated into control unit 110 to reduce the weight of the headset. Plus power supplies will be incorporated into control unit 110, rather than in PDT devices 106a and 106b. It is envisioned that a further reduction in weight could be achieved by locating the light sources within control unit 110 and using one or more fiber optic cables (not shown) to convey the light emitted by the light sources to PDT devices 106a and 106b. However, this option may not result in a significant decrease in weight, since it is envisioned that the light sources used will be relatively lightweight LEDs. Another contemplated embodiment would provide for running control cables 108a and 108b alongside the left and right earpieces of the headset and disposing control unit 110 at the rear of the headset. While this modification would increase the weight of the headset, it would result in a headset in which control cables 108a or 108b are less likely to become tangled, disconnected, or broken.

FIG. 16 illustrates a slit lamp 120 that has been modified to include a PDT treatment unit 130, corresponding to any of the embodiments of the PDT devices described above (except the headsets). In general, a slit lamp is a table mounted unit that includes a chin rest and head rests to hold a patient's head stationary so that precise targeting of light or examination within a patient's eyes may be achieved. In FIG. 16, PDT treatment unit 130 is targeted at macula 18 of eye 10. It is envisioned that any of the PDT devices described above with respect to FIGS. 2–11C could be used for PDT treatment unit 130.

Figure 17:
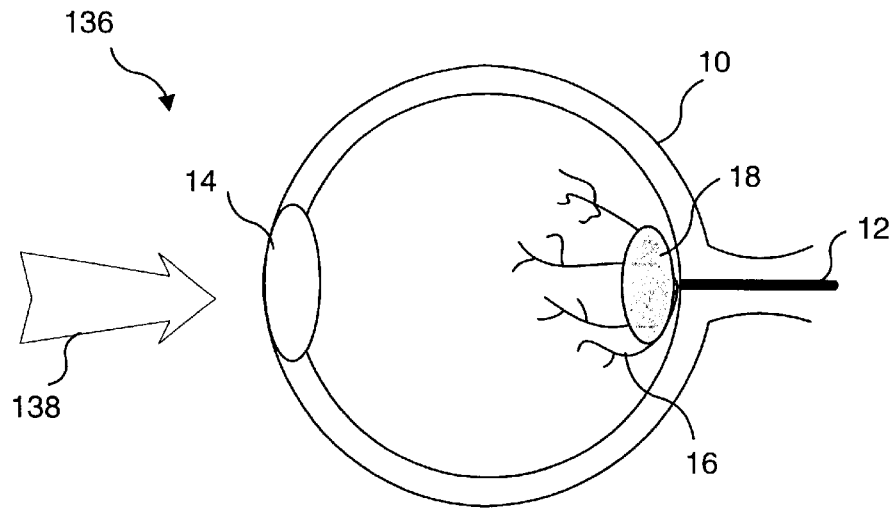
FIG. 17 is a schematic view of a method of delivering non-coherent light to a treatment site in the eye using a direct approach that results in the light entering the eye through the lens of the eye.

Light having a wavelength that corresponds to the absorption waveband of the photoreactive agent can be directed at the treatment site or target region in the macula (or at any other desired target region) either directly through the lens and cornea of the eye or indirectly, along paths that do not pass through the eye's lens or cornea. FIG. 17 schematically illustrates the direct approach. In FIG. 17, light of the appropriate waveband is directed at the treatment region from the front of the eye, as indicated by an arrow 138. The light passes through lens 14 in the eye and proceeds to a target area, preferably in macula 18.

Figure 18:
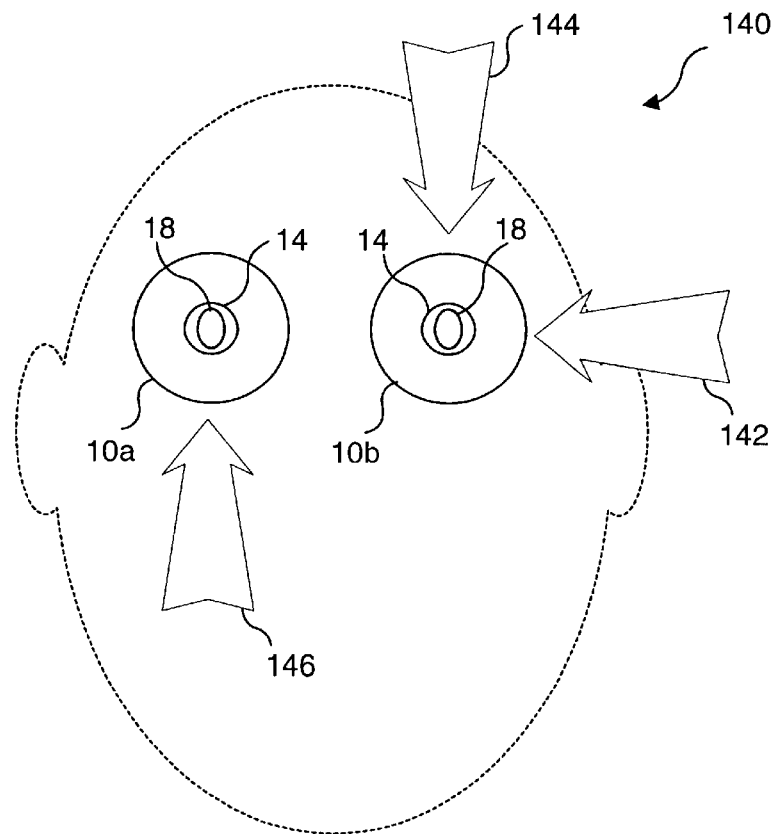
FIG. 18 is a schematic view of methods of delivering non-coherent light to a treatment site in the eye using indirect approaches that result in the light entering the eye transcutaneously.

FIG. 18 illustrates several indirect paths for targeting the macula (or other region of interest in the eye). These indirect paths include a lateral orbital approach 142, a superior orbital approach 144, and an inferior orbital approach 146. Light following each of these indirect paths passes into the eye transcutaneously, passing through an orbital wall. When following such an indirect path, the light illuminates the area of pathology in a more diffuse manner than when administered along the direct path. It is envisioned that light administered along an indirect path be administered from a light source included in a PDT device on a headset, generally like those described above. Although the headsets described above are adapted to administer light into the patient's eye(s) along a direct path, as illustrated in FIG. 17, PDT devices attached to headsets can readily be configured to provide light administered along the inferior, superior, and lateral approaches illustrated in FIG. 18. For instance, a headset for administering light from PDT devices utilizing superior approach 144 could be fabricated in the form of a headband, in which the PDT devices are disposed on the patient's forehead above each eye. A PDT headset utilizing lateral orbital approach 142 could be provided by mounting PDT devices on the arm or ear pieces of the headset, generally between the patient's ears and the front lenses of the headset. Inferior orbital approach 146 can be achieved by mounting the PDT devices below the lenses of the headset, such that the PDT devices rest on the patient's cheeks.

The Incorporation of Lenses into the Preferred Embodiments

It should be noted that a plurality of different lenses can be beneficially employed to selectively focus the light emitted from a light source. It is anticipated that lens configurations such as convergent lenses, totally internally reflective lenses, divergent lenses, and a plurality of lenses in combination can be employed in conjunction with the present invention. Those of ordinary skill in the art will readily understand how these types of lenses can be incorporated in the above described embodiments.

Targeted PDT Therapy

The effects of the light therapy on normal tissue that has absorbed the photoreactive agent may range from mild reddening of the tissue to severe tissue damage, depending on the amount of light delivered to the normal tissue, and the amount of the photoreactive agent absorbed by the normal tissue. One method to reduce the risk of incidental damage to non target tissue is to provide a highly focused pattern of light that irradiates only the target tissue (such as abnormal neovascular). Various of the embodiments described above can be beneficially employed to provide such a highly focused light pattern. Another method to minimize damage to the normal tissue is to substantially reduce the extent to which normal tissue absorbs the photoreactive agent.

One approach developed to ensure that the photoreactive agent is preferentially absorbed by the target tissue, rather than by normal tissue, is to bind antibodies to a photoreactive agent, such that the antibodies are targeted to the abnormal cells at a treatment site. When a photoreactive agent conjugated with an antibody is administered to a patient, the antibodies will tend to bind the photoreactive agent to the abnormal tissue, but not to normal tissue, thereby improving the specificity of the PDT and avoiding harm to the normal tissue. Those of ordinary skill in the art will readily recognize that an antibody specific to abnormal target tissue within the eye can be conjugated with a selected photoreactive agent, to provide for the preferential absorption of the photoreactive agent by the abnormal tissue, thereby minimizing the risk of damage to non target tissue.

Although the present invention has been described in connection with several preferred forms of practicing it and modifications thereto, those of ordinary skill in the art will understand that many other modifications can be made to the invention within the scope of the claims that follow. Accordingly, it is not intended that the scope of the invention in any way be limited by the above description, but instead be determined entirely by reference to the claims that follow.

The invention in which an exclusive right is claimed is defined by the following:

1. A light therapy device for treating a disease of the eye, comprising:
   (a) a power source that provides electrical energy;
   (b) at least one non-coherent light source coupled to said power source and adapted to be energized thereby; said light source, when energized, producing light within a waveband corresponding to an activation waveband of a photoreactive agent disposed at a treatment site within the eye; and
   (c) at least one focusing lens adapted to convey light emitted by the non-coherent light source to the treatment site in the eye, said light activating the photoreactive agent to treat the disease.

2. The device of claim 1, further comprising a mirror positioned adjacent to said at least one light source so as to reflect the light emitted by said light source onto the focusing lens, which is disposed between said light source and the eye.

3. The device of claim 1, wherein said at least one light source is one of a light emitting diode (LED), an incandescent bulb, a halogen bulb, a chemical luminescence, a vacuum fluorescence, a radio frequency excited gas, a microwave excited gas, and a cold cathode fluorescent tube.

4. The device of claim 3, wherein said at least one light source comprises an LED, and the light emitted by said LED is in a waveband that includes at least one of a red light and a blue light.

5. The device of claim 1, wherein the light source comprises a laser diode array that generates non-coherent light.

6. The device of claim 1, wherein said at least one focusing lens includes one of a divergent lens, a convergent lens, and a totally internally reflective lens.

7. The device of claim 1, further comprising a headset that includes a supporting frame for mounting said at least one non-coherent light source and said at least one focusing lens adjacent to a patient's eye.

8. The device of claim 1, wherein said at least one focusing lens collimates light from said at least one light source onto a macular region of the eye.

9. The device of claim 1, wherein said at least one focusing lens is adapted to focus light from said at least one light source onto an area that is smaller in size than a macular region of the eye.

10. The device of claim 1, further comprising a filter, said filter comprising a first portion that blocks the light in the waveband corresponding to the activation waveband of the photoreactive agent, and a second portion that transmits the light in the waveband corresponding to the activation waveband of the photoreactive agent, said filter being disposed between said at least one light source and the eye.

11. The device of claim 10, wherein a shape of an area of the light focused by said at least one focusing lens corresponds to a shape of said second portion of said filter, and the filter is selected so that the shape of the area corresponds to a shape of a diseased region in the eye.

12. The device of claim 11, wherein at least one of said first portion of said filter and said second portion of said filter is able to change from a first state that transmits the light in the waveband corresponding to the activation waveband of the photoreactive agent, to a second state that blocks the light in the waveband corresponding to the activation waveband of the photoreactive agent.

13. The device of claim 12, wherein the change in state is in response to one of an electrical stimulus and a thermal stimulus.

14. The device of claim 13, wherein said first portion of the filter comprises one of a liquid crystal material and a piezoelectric ceramic material.

15. The device of claim 1, wherein a disposition within the eye of a focal point of the light emitted by said at least one light source focused by said at least one focusing lens is varied by changing a position of at least one of said at least one light source and said at least one focusing lens.

16. The device of claim 1, wherein said at least one focusing lens comprises a plurality of focusing lenses of different focal lengths, and wherein a disposition within the eye of a focal point of light emitted by said at least one light source is varied by causing the light emitted by the at least one light source to be conveyed to the eye by a different one of said plurality of focusing lenses.

17. The device of claim 1, wherein said at least one focusing lens comprises a deformable material such that its focal point varies as said at least one focusing lens is deformed; further comprising means to deform said at least one focusing lens to vary the focal point.

18. The device of claim 17, wherein said means comprises one of a mechanical actuator, a hydraulic actuator, and an electrical actuator.

19. The device of claim 1, further comprising a filter that blocks the light in the waveband corresponding to the activation waveband of the photoreactive agent, said filter being selectively moveable between a first position in which the filter is not within an optical path between said at least one light source and the eye, and a second position in the optical path.

20. The device of claim 1, wherein said at least one light source comprises a first light source that does not emit the light within the waveband corresponding to the activation waveband of the photoreactive agent, and a second light source that does, said first and second light sources being disposed such that a first focal point of the light emitted by said first light source and focused by said at least one focusing lens substantially overlaps a second focal point of the light emitted by said second light source and focused by said at least one focusing lens, such that when said first light source is energized and said second light source is not energized, the position of the first focal point is selectively targeted toward a desired treatment site in the eye without activating the photoreactive agent, the second light source being then energized to activate the photoreactive agent at the desired treatment site, without activating any photoreactive agent at other sites within the eye.

21. The device of claim 1, wherein said at least one light source comprises a first light source that emits light in a waveband that is unable to penetrate deep into tissue, and a second light source that emits light in a waveband that is able to penetrate substantially deeper into the tissue.

22. The device of claim 1, further comprising an ophthalmologic slit lamp housing in which said at least one light source and said at least one focusing lens are disposed.

23. The device of claim 1, wherein said at least one focusing lens is adapted to be positioned in front of a lens of a patient's eye to focus the light emitted by said at least one light source through the lens of the patient's eye.

24. The device of claim 1, wherein said at least one focusing lens is adapted to be positioned to focus the light emitted by said at least one light source into a patient's eye transcutaneously along one of a lateral orbital path, an inferior orbital path, and a superior orbital path.

25. The device of claim 1, wherein the disease of the eye treated by the light includes one of a macular degeneration and a diabetic retinopathy.

26. The device of claim 1, wherein said at least one focusing lens comprises a lens whose focal point can be selectively varied.

27. A method for using non-coherent light based photodynamic therapy to treat a disease condition of the eye, the method comprising the steps of:
   (a) providing a photodynamic therapy device that includes at least one non-coherent light source that emits light in a wavelength that activates a photoreactive agent;
   (b) administering the photoreactive agent to a patient;
   (c) energizing the light source such that non-coherent light is emitted thereby; and
   (d) positioning said photodynamic therapy device adjacent to an eye to be treated, such that light emitted by said at least one non-coherent light source is directed into the eye by said photodynamic therapy device, said light activating the photoreactive agent, causing a desired therapeutic change in a diseased treatment site within the eye.

28. The method of claim 27, wherein the disease condition relates to a choroidal neovasculature associated with age-related macular degeneration (AMD).

29. The method of claim 27, wherein the photoreactive agent is preferentially absorbed by diseased tissue in the eye, and the step of positioning the photodynamic therapy device comprises the step of placing the photodynamic therapy device such that non-coherent light emitted by said at least one non-coherent light source is directed into the eye transcutaneously by one of a lateral orbital approach, an inferior orbital approach, and a superior orbital approach.

30. The method of claim 29, wherein the light emitted by said at least one non-coherent source is directed toward the macular region of the eye.

31. The method of claim 29, wherein a wavelength of the light used to activate the photoreactive agent is sufficiently long to penetrate tissue to a substantial depth.

32. The method of claim 31, wherein the light is at least one of red, blue, and a mixture of red and blue.

33. The method of claim 27, wherein the photodynamic therapy device further includes a headset, and wherein the step of positioning the photodynamic therapy device comprises the step of placing the headset on a patient's head.

34. The method of claim 27, wherein said at least one non-coherent light source comprises one of a light emitting diode (LED), an incandescent bulb, a halogen bulb, a chemical luminescence, a vacuum fluorescence, a radio frequency excited gas, a microwave excited gas, a laser diode array and a cold cathode fluorescent tube.

35. The method of claim 27, wherein the photodynamic therapy device further comprises a reflector.

36. The method of claim 27, wherein said at least one light source comprises a first light source that emits a first waveband of light that will activate the photoreactive agent, and a second light source that emits a second, different waveband of light that will activate the photoreactive agent, and the step of energizing the photodynamic therapy device comprises energizing at least one of the first light source and the second light source.

37. The method of claim 36, wherein the first light source emits blue light and the second light source emits red light.

38. The method of claim 27, wherein the photodynamic therapy device further comprises means for focusing the light emitted by said at least one non-coherent light source at a discrete focal point, the step of positioning the photodynamic therapy device comprising the step of directing the discrete focal point onto the diseased treatment site within the eye.

39. The method of claim 38, wherein said at least one light source emits a first wavelength of light that does not activate the photoreactive agent, the step of directing the discrete focal point comprising the steps of:

(a) energizing said at least one non-coherent light source so that only said first wavelength of light is directed into the eye; and (b) positioning the discrete focal point of the light emitted at said first wavelength onto the diseased treatment site to facilitate aiming the second light source.

40. The method of claim 27, wherein the photodynamic therapy device is included in a slit lamp housing.

41. The method of claim 27, wherein the photodynamic therapy device further comprises means for focusing the light emitted by said at least one non-coherent light source at a discrete focal point, the step of positioning the photodynamic therapy device comprising the step of overlapping successive positions of the discrete focal point on the diseased treatment site within the eye.

42. The method of claim 41, wherein the photodynamic therapy device further comprises a plurality of focusing lens having different focal lengths, and the step of overlapping the successive positions of discrete focal points onto the diseased treatment site within the eye comprises the steps of:

(a) selecting a focusing lens having a discrete focal point lying within the diseased treatment site; and (b) using only the focusing lens that was selected to direct the light emitted by said at least one non-coherent light source into the eye.

43. The method of claim 42, wherein:

(a) the photodynamic therapy device further comprises:
   (i) a focusing lens made of a deformable material, such that deforming the focusing lens changes its focal point; and
   (ii) means to deform said lens; and (b) the step of overlapping comprises the step of deforming the lens to focus the light onto the diseased treatment site.

44. The method of claim 42, wherein:

(a) the photodynamic therapy device further comprises a plurality of filters, each of said plurality of filters comprising a first portion that blocks the waveband of light that activate the photoreactive agent, and a second portion that transmits the waveband of light that activates the photoreactive agent, and each filter having a differently sized and/or shaped second portion; and (b) the step of overlapping the discrete focal point on the diseased treatment site within the eye comprises the step of selecting a filter from the plurality of filters that most closely produces a sized and shaped focal point corresponding to a shape of the diseased treatment site to limit an area of the eye to which the light is applied to that of the diseased treatment site.

45. The method of claim 27, further comprising the steps of:

(a) providing a filter having a first portion and a second portion; and (b) changing at least one of said first portion of said filter and said second portion of said filter from a first state that transmits the light in the waveband that activates the photoreactive agent, to a second state that blocks the light in the waveband that activates the photoreactive agent.

\* \* \* \* \*